United States Patent [19]
Knauer et al.

[11] Patent Number: 6,095,146
[45] Date of Patent: Aug. 1, 2000

[54] GLOW-IN-THE-DARK HEARING PROTECTIVE DEVICES

[75] Inventors: Richard Knauer; Brian Myers, both of Indianapolis, Ind.; James Hall, Lincoln, R.I.

[73] Assignee: Aearo Company, Southbridge, Mass.

[21] Appl. No.: 09/357,037

[22] Filed: Jul. 20, 1999

[51] Int. Cl.$^7$ .................................................. A61F 11/00
[52] U.S. Cl. ................................ 128/864; 2/209; 2/171; 2/DIG. 11; 128/866
[58] Field of Search ................................... 128/864–868; 2/171, 209, DIG. 11

[56] References Cited

U.S. PATENT DOCUMENTS

| | | | |
|---|---|---|---|
| 3,661,225 | 5/1972 | Anderson | 128/866 |
| 4,461,290 | 7/1984 | Gardner | 128/866 |
| 4,490,857 | 1/1985 | Leight | 128/866 |
| 5,749,373 | 5/1998 | Dix | 128/866 |
| 6,006,361 | 12/1999 | Falco | 128/866 |

*Primary Examiner*—Michael A. Brown
*Attorney, Agent, or Firm*—Cantor Colburn LLP

[57] ABSTRACT

Hearing protective devices having glow-in-the-dark properties are presented in the present invention. In an exemplary embodiment, the hearing protective device comprises a semi-aural device, an earplug, or an earmuff device. In all embodiments, a glow-in-the-dark material is incorporated into at least a part of the hearing protective device so that the glow-in-the-dark material continues to emit light for an extended period of time in a dark environment after the material has been excited by irradiation. Preferred and exemplary glow-in-the-dark materials comprise phosphorescent materials. The glow-in-the-dark materials may be disposed on a surface of the hearing protective part or dispersed throughout the material which forms this part.

25 Claims, 2 Drawing Sheets

GLOW-IN-THE-DARK HEARING PROTECTIVE DEVICES

FIELD OF THE INVENTION

This invention relates generally to hearing protective devices and more particularly, to hearing protective devices having glow-in-the-dark properties.

BACKGROUND OF THE INVENTION

Environmental sounds are typically comprised of a mixture of various sound wave frequencies having varying intensities. It is well documented that repeated or prolonged exposure to sounds of sufficiently high sound pressure level will cause temporary or permanent hearing loss. For example, exposure to sound waves of some frequencies and of varying intensities under conditions of severe impact can damage the auditory organ and cause serious hearing problems, including deafness. Injurious noises such as those caused by explosions or bursts are often comprised of a mixture of sound wave frequencies of varying intensity. These disturbing frequencies are in both the high and low frequency bands and have an intensity sufficient to cause hearing problems. Individuals who are frequently exposed to sound having such disturbing and sometimes dangerous frequencies and intensities run the risk of incurring such injuries as hearing loss or even deafness. These individuals include workers at demolition or construction sites, operators of heavy, noisy equipment and those in active military service. Ear (i.e. hearing) protection is needed to prevent a loss in hearing acuity and the gradual increase in the threshold of hearing resulting from extended exposures to loud noise.

Hearing protectors fall generally into three categories, including protectors that cap the entrance to the ear canal; protectors which enter the ear canal and seal the ear canal prior to the bend in the ear canal (usually referred to simply as semi-insert devices); and protectors that enter the ear canal and take the bend in the ear canal (sometimes referred to as banded earplugs). Semi-insert hearing protectors generally protect similarly to earplugs, but usually to a lesser level. Semi-insert hearing protectors are also referred to as semi-aural hearing protectors. As used herein, "hearing protective devices" refers generally to hearing protectors falling into one of the three categories described above. Hearing protective devices are designed to reduce the negative effects of exposure to dangerous frequencies by limiting the entry of all sound waves into the auditory organ.

Hearing protective devices are worn in a wide variety of environments. In many instances, these hearing protective devices are worn in dark or limited light environments. When the hearing protective devices are worn in a dark environment, there are additional factors which should be considered. For example, because the hearing protective devices are designed to attenuate noise, there is an increased chance that an individual in a given environment may not be aware of events that are happening around the wearer, especially when it is dark out and the eyesight of the wearer is limited due to the darkness. It is also accordingly, more difficult to locate objects that are laid down or accidently dropped in a dark environment.

It would be advantageous to provide a hearing protective device which offers advantages from both a safety and a convenience point of view when the hearing protective device is worn in a dark or limited light environment.

SUMMARY OF THE INVENTION

The above-discussed and other drawbacks and deficiencies of the prior art are overcome or alleviated by the hearing protective devices of the present invention which have a glow-in-the-dark property. In an exemplary embodiment, the hearing protective device comprises a semi-aural device, an earplug, or an earmuff device. In all embodiments, a glow-in-the-dark material is incorporated into at least a part of the hearing protective device so that the glow-in-the-dark material continues to emit light for an extended period of time in a dark environment after the material has been excited by irradiation. Preferred and exemplary glow-in-the-dark materials comprise phosphorescent materials.

One advantage of the present invention is that in terms of safety, a glow-in-the-dark hearing protective device can aid in an ability to spot where an individual is located in a dark or limited light environment. This provides increased awareness of the presence of the individual wearing the glow-in-the-dark hearing protective device. In addition, if the hearing protective device is accidently dropped or laid down, it is easily located in the dark environment when it has a glow-in-the-dark property. Furthermore, the present invention also makes supervision of employee compliance with hearing protection regulations much easier in a dark environment because the determination of whether an employee is wearing a hearing protective device is more evident in a dark environment if the hearing protective device has a glow-in-the-dark property. In extreme cases, such as mining or caving accidents, the glow-in-the-dark hearing protective device of the present invention could actually be a life saver by helping identify the location of an individual in a more time efficient manner and thereby increase the chances that the individual may receive more prompt medical attention.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES.

DESCRIPTION OF THE PREFERRED EMBODIMENTS

The present invention broadly comprises hearing protective devices having a glow-in-the-dark material disposed therein so that a portion of the hearing protective device continues to emit light for an extended period of time after excitation of the material. This results in the material glowing in the dark after the material has been activated by radiant energy.

Figure 1:
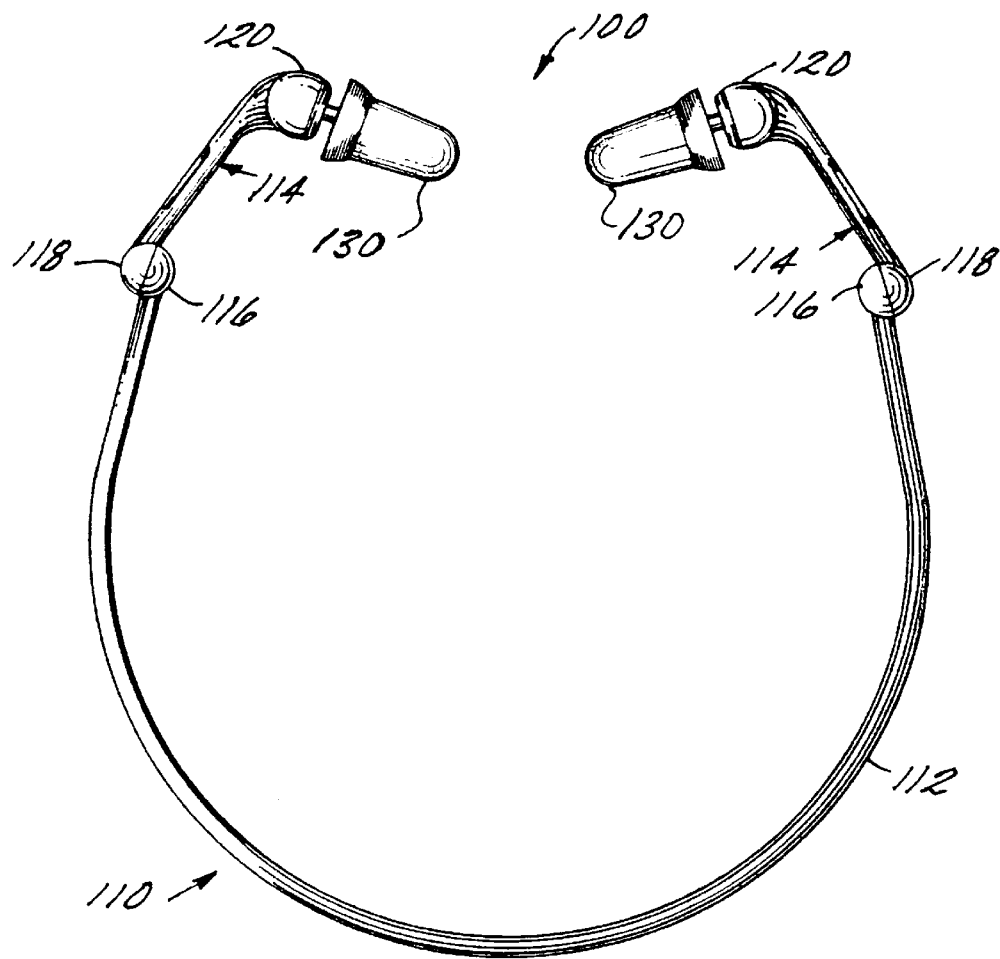
FIG. 1 is front elevation view of an exemplary semi-aural device of the present invention.

Now turning to FIG. 1 in which the hearing protective device comprises a semi-aural device generally indicated at 100. FIG. 1 is a front view of an exemplary semi-aural device 100. Semi-aural device 100 includes a frame 110 having a band 112 and a pair of legs shown generally at 114. Band 112 is generally U-shaped and is made from a resilient flexible material such as a plastic. Band 112 has two leg supports 116, each of which forms one half of a swivel or rotating joint between band 112 and leg 114. Leg support 116 is integral with band 112 and in an exemplary embodiment is a spherical segment. The flat faces of a first leg end 118 and leg support 116 are placed opposite each other to form a swivel joint. The swivel joint allows first leg end 118 to rotate relative to leg support 116 thereby allowing leg 114 to rotate relative to band 112. Leg 114 includes a second leg end 120 for receiving a hearing protector 130. In an exemplary embodiment, the second leg end 120 is a spherical segment. It will be appreciated that second leg end 120 may comprise any other desired functional shape such as ovular, triangular, etc. The outer dimension of second leg end 120 is preferably equal to the average concha bowl openings so that second leg end 120 cannot be inserted into the ear canal but is preferably insertable (and rests in) the concha bowl (so that a hearing protector 130 attached to end 120 is permitted to freely articulate in the ear canal). Second leg end 120 includes an opening formed therein which receives hearing protective device 130. FIG. 1 shows one exemplary hearing protective device 130 and it is understood that hearing protective device 130 may be protectors that cap the entrance to the ear canal; protectors which enter the ear canal and seal the ear canal prior to the bend in the ear canal; or protectors that enter the ear canal and take the bend in the ear canal.

In accordance with the present invention, band 112 and/or the pair of legs 114 are made glow-in-the-dark by integrating glow-in-the-dark material into band 112 and/or the pair of legs 114 during the fabrication thereof. For the purpose of illustration only, the glow-in-the-dark material will be discussed as being integrated into band 112; however, it is understood that the glow-in-the-dark material can likewise be integrated into the pair of legs 114 so that both the pair of legs 114 and band 112 contain glow-in-the-dark material or just the pair of legs 114 contains glow-in-the-dark material. The glow-in-the-dark material may be disposed on an outer surface of band 112 or alternatively the glow-in-the-dark material may be disposed throughout the material, e.g., resin, forming band 112 so long as any covering material which is used is sufficiently transparent at the appropriate wavelengths so that excitation of the luminescent material is possible and the emitted glow in clearly visible when irradiated and viewed through the covering material.

As used herein, "glow-in-the-dark material" refers to any material which have the property of continuing to emit light for an extended period of time after excitation, e.g., by subjecting the material to appropriate wavelengths of light.

Exemplary glow-in-the-dark materials include phosphorescent materials which have the property of continuing to emit light for an extended period of time after excitation. Phosphorescent materials include a phosphor which has been artificially prepared and has the property of luminescence when activated by appropriate wavelengths of light. A variety of phosphors are available for use in providing luminescence when activated by an appropriate light source. Commercially available phosphors include zinc sulfide, zinc cadmium sulfide, alkaline earth sulfides with or without a trace of activators, such as silver, copper, or manganese to provide the desired rapid activation of the phosphorescence material on providing the luminescent image.

One preferred glow-in-the-dark material is a zinc sulfide material. Zinc sulfide materials are commercially available from a number of suppliers. Zinc sulfide material is commonly available as an additive which is easily added to resins used to form the glow-in-the-dark plastic components of the hearing protective devices of the present invention, including band 112 and the pair of legs 114 of earmuff device 10.

Band 112 is formed of suitable materials including thermoplastic materials. In an exemplary embodiment, band 112 is formed of a material selected from the group consisting of polyvinyl chloride, ABS, polypropylene, and polyethylene and a phosphorescent material which in one embodiment is added to the resin used to make band 112. Preferably, the phosphorescent material comprises a zinc sulfide material. One exemplary zinc sulfide material is commercially available from C. Withington, Co. Inc. under the trade name Excite 2330 LBY. A predetermined amount of phosphorescent material is added to the resin so that band 112 has a sufficient level of luminescence when the phosphorescent material is activated. In one exemplary embodiment, the phosphorescence material in the form of a zinc sulfide pigment was added to the resin so that the zinc sulfide material was present in an amount from about 3% to about 25% by weight of the total composition, more preferably from about 8% to about 10%. It being understood that the above-recited range is merely exemplary in nature and it will be appreciated that depending upon the precise makeup band 112 and the phosphorescent material used, other ranges are within the scope of the present invention so long as band 112 has a sufficient amount of phosphorescent material that it has a glow-in-the-dark property when activated. Band 112 is then formed using conventional methods such as a molding process. The resulting band 112 retains its typical properties but also exhibits a glow-in-the-dark property. Accordingly, when band 112 is subjected to a light source, energy activates the glow-in-the-dark material and when band 112 is subsequently placed in a dark environment, glowing light will emit from band 112 and will be sustained for a period of time It is also within the scope of the present invention that the phosphorescent material may be applied to an outer surface of band 112 using a conventional post treatment process. In this embodiment, the phosphorescent material is preferably placed in a suitable carrier and disposed on the outer surface of band 112 to produce glow-in-the-dark band 112.

Figure 2:
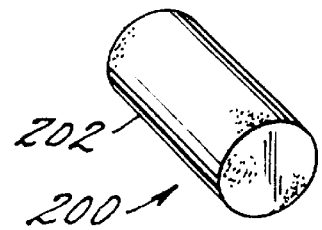
FIG. 2 is a perspective view of an exemplary earplug of the present invention.

Referring to FIG. 2 in which the present invention is shown embodied in a hearing protective device in the form of an earplug. An exemplary earplug is generally indicated at 200 and it is understood that the earplug 200 is shown for purpose of illustration and not limitation. It is this within the spirit and scope of the present invention that any number of foam earplugs 200 may be used according to the present invention. Earplug 200 has a body 202 which is formed of a suitable foam material. Suitable foams include those foams selected from the group consisting of polyurethane, acrylic, polyvinyl chloride, acrylic blends, or mixtures thereof. In an exemplary embodiment, earplug 200 comprises a foam made from a polyurethane material and in particular, preferred polyurethane formulations are disclosed in commonly assigned U.S. Pat. No. 5,792,998 to Gardner, Jr. et al., which is hereby incorporated in its entirety.

In this third embodiment, suitable glow-in-the-dark materials include phosphorescent pigments which are added to the polyurethane foam formulations during manufacturing of earplug 200. In one exemplary embodiment, glow-in-the-dark earplug 200 is produced by adding a predetermined amount of a suitable phosphorescent material, e.g., a zinc sulfide material, to the aqueous side of the mixture used to form earplug 200. The aqueous side is then intermixed with a hydrophilic prepolymer material, such as Hypol which is commercially available from Dow Chemical, resulting in the phosphorescent material being dispersed throughout the entire earplug 200. For example, a commercially available zinc sulfide material was added to the aqueous side of a polyurethane mixture. The amount of zinc sulfide material added was from about 3% to about 25% by weight of the total polyurethane composition, more preferably from about 8% to about 10%. It being understood that these ranges are not limiting of the present invention and are included for purpose of illustration of the present invention.

Figure 3:
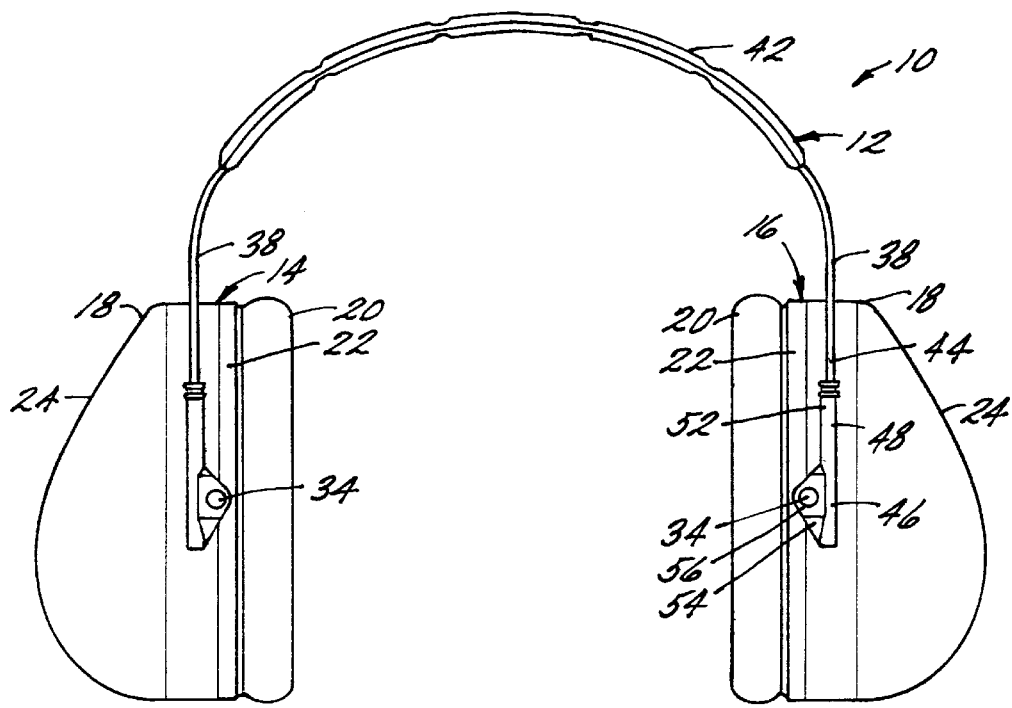
FIG. 3 is a front elevation view of an exemplary acoustic earmuff device of a first embodiment of the present invention.

In one exemplary embodiment shown in FIG. 3, a hearing protective device in the form of an acoustic earmuff device is presented and generally indicated at 10. Acoustic earmuff device 10 broadly comprises a generally U-shaped, resilient connecting band 12 and a pair of acoustic earmuffs 14 and 16 connected to opposite ends of connecting band 12. Each of acoustic earmuffs 14 and 16 comprises a rigid earcup 18, a foam cushion 20, and optionally an earmuff cup liner 22. Earmuff cup 18 is generally formed of two pieces, a cup shaped portion 24 and a cushion sealplate (not shown) which are ultrasonically sealed together at an interface therebetween. In the exemplary embodiment shown in FIG. 3, cup shaped portion 24 includes a pair of spaced retaining pins 34 which extend outwardly from an outer surface of cup shaped portion 24. Retaining pins 34 are preferably spaced about 180° from one another and are centrally located around a peripheral edge of cup shaped portion 24. It being understood that retaining pins 34 may have a variety of cross-sectional shapes and in the exemplary embodiment shown, retaining pins 34 are generally circular in shape.

In the exemplary embodiment shown in FIG. 3, connecting band 12 comprises two generally parallel disposed, resilient wires 38 held in substantially parallel alignment by a strip 42 of flexible material, such as a rubber or a plastic. Each end 44 of resilient wires 38 includes a connector member 46 which includes a base portion 48 having a central opening extending therethrough. The central opening receives end 44 of one of wires 38 so that end 44 frictionally is retained within the central opening of base portion 48. Formed within the central opening at an upper end 52 is a stopper (not shown) which permits end 44 of resilient wire 38 to freely move within the central opening but prevents end 44 from being removed from the central opening at upper end 52.

Connecting member 46 has an ear 54 extending from base portion 48, wherein ear 54 has an opening 56 which is sized to receive retaining pin 34 so that ear 54 frictionally engages and retains pin 34. As a result, ends 44 of wires 38 are secured to earmuff cups 14 and 16 by the intimate coupling between connector member 46 and retaining pin 34. It will now be understood that earmuffs understood that end 44 is free to slide within the central opening so that acoustic earmuff 14 and 16 may be slidably adjusted with respect to connecting band 12 so as to dispose them around the ears and resiliently against the head of a wearer. It being understood that any number of connecting bands 12 may be used in earmuff device 10 of the present invention and the illustrated connecting band 12 is merely illustrates one type of connecting band 12 which may be used.

Cushion 20 is generally formed of a plurality of thin sheets of flexible polyvinyl chloride or polyurethane, one of the sheets being vacuum formed and filled with a foam or a liquid, then thermally bonded to a second sheet, after which the trim is cut off. It being understood that other types of cushions 20 may be used with the earmuff cups 14 and 16 of the present invention. The shape of cushion 20 may be cylindrical, round, or rectangular to fit the generally matching earmuff cup 14 and 16 design in a reasonable manner. Cushion 20 is quite flexible and may also be made to a shape requiring deformation to fit earmuff cup 14 and 16. One exemplary and preferred cushion 20 is disclosed in commonly assigned U.S. Pat. No. 5,420,381 to Gardner Jr. et al., which is hereby incorporated in its entirety.

Optional earmuff cup liner 22 generally comprises an open cell foam or other material containing open pores of size and shape to absorb high frequency sound of about 1000 to about 8000 Hertz. Typically, polyurethane open-celled acoustical foam is used because of its low cost and low density.

In accordance with the present invention, at least a portion of earmuff device 10 has a glow-in-the-dark property. In the exemplary embodiment shown in FIG. 3, cup shaped portion 24 is made glow-in-the-dark by disposing a glow-in-the-dark material into the material forming cup shaped portion 24. The glow-in-the-dark material may be disposed on outer surface 32 of cup shaped portion 24 or alternatively the glow-in-the-dark material may be dispersed throughout the material forming cup shaped portion 24 so long as any covering material which is used is sufficiently transparent at the appropriate wavelengths so that excitation of the luminescent material is possible and the emitted glow in clearly visible when irradiated and viewed through the covering material. Typically, cup shaped portion 24 is formed of a plastic material such as polyvinyl chloride, acrylonitrile butadiene styrene (ABS), polypropylene, or polyethylene.

Figure 4:
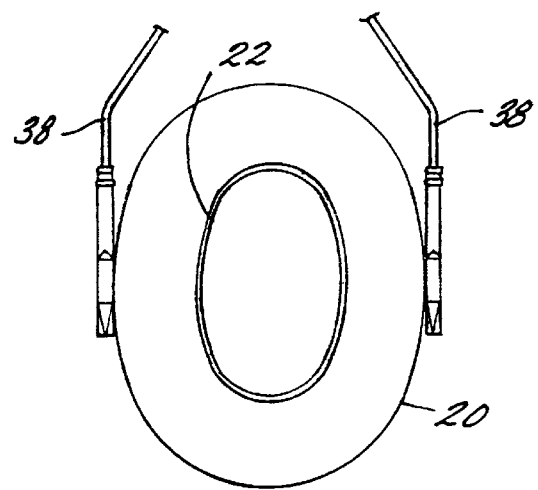
FIG. 4 is a side elevation view of a portion of an exemplary acoustic earmuff device of a second embodiment of the present invention.

FIG. 4 shows an earmuff device of a second embodiment and is generally indicated at 10'. In this embodiment, earmuff device 10' is very similar to earmuff device 10 of FIG. 1 with the exception that the glow-in-the-dark material is disposed on an outer surface of earmuff cushion 20 or dispersed throughout the material forming earmuff cushion 20. The glow-in-the-dark material may be disposed on the outer surface of earmuff cushion 20 by conventional post treatment processing techniques, wherein the glow-in-the-dark material is provided in a carrier and directly disposed to the outer surface of earmuff cushion 20.

Referring to FIGS. 3 and 4, glow-in-the-dark material may be easily excited by exposing and/or subjecting and/or irradiating earmuff device 10 or 10' to a light source, e.g., incandescent lamp, day light, or a black light. During use after earmuff device 10 or 10' has been subjected to the light source, energy will activate the glow-in-the-dark material, e.g., phosphorescence material. When earmuff device 10 or 10' is placed in a dark environment, glowing light will emit from cup shaped portion 24 of earmuff device 10 and cushion 20 of earmuff device 10'. An observer in the dark would be able to see the corresponding glow-in-the-dark part of either earmuff device 10 or 10'. The glow-in-the-dark material will be sustained in the darkness for a period of time.

Many phosphorescent materials and more particularly phosphors are commercially available and emit different colors and continue to emit radiation for different periods of time after they are removed from ambient light. Accordingly, the selection of particular phosphors or combination of phosphors to provide predetermined characteristics is another factor that can be employed in the present invention to create different kinds of phosphorescent hearing protective devices.

The present invention provides hearing protective devices offering advantages from both a safety and a convenience point of view due to the glow-in-the-dark property exhibited by the hearing protective devices. One advantage of the present invention is that in terms of safety, a glow-in-the-dark hearing protective device can aid in an ability to spot where an individual is located in a dark environment. This provides increased awareness of the presence of the individual wearing the glow-in-the-dark hearing protective device. In addition, if the hearing protective device is dropped or laid down, it is easily located in the dark environment when it has a glow-in-the-dark property. Furthermore, the present invention also makes supervision of employee compliance with hearing protection regulations much easier in a dark environment because the determination of whether an employee is wearing a hearing protective device can be more evident in a dark environment if the hearing protective device has a glow-in-the-dark property. In extreme cases, such as mining or caving accidents, the glow-in-the-dark hearing protective device of the present invention could actually be a life saver by helping identify the location of an individual in a more time efficient manner and thereby increase the chances that the individual may receive more prompt medical attention.

While preferred embodiments have been shown and described, various modifications and substitutions may be made thereto without departing from the spirit and scope of the present invention. Accordingly, it is understood that the present invention has been described by way of illustrations and not limitation.

What is claimed is:

1. A phosphorescent hearing protective device comprising:
   a frame having a pair of distal ends, each of the ends having an opening formed therein; and
   a hearing protector mounted to each of the ends, wherein the frame includes a phosphorescent material, the phosphorescent material being activated by radiant energy to glow-in-the-dark.

2. The phosphorescent hearing protective device of claim 1, wherein the frame is formed of a resilient material.

3. The phosphorescent hearing protective device of claim 2, wherein the resilient material is selected from the group consisting of ABS, polyvinyl chloride, polypropylene, and polyethylene.

4. The phosphorescent hearing protective device of claim 1, wherein the phosphorescent material is disposed on a surface of the frame.

5. The phosphorescent hearing protective device of claim 1, wherein the phosphorescent material is dispersed throughout the frame.

6. The phosphorescent hearing protective device of claim 1, wherein the radiant energy is selected from the group consisting of incandescent light, daylight, and ultraviolet light.

7. The phosphorescent hearing protective device of claim 1, wherein the phosphorescent material is a zinc sulfide material.

8. The phosphorescent hearing protective device of claim 1, wherein the hearing protector is selected from the group consisting of an ear cap, a semi-insert device, earplug, and a protector having a foam portion connected to a stem.

9. The phosphorescent hearing protective device of claim 1, wherein the phosphorescent material is present in an amount from about 3% to about 25% by weight of the total composition.

10. A phosphorescent hearing protective device comprising:
    a band having a pair of ends;
    a pair of legs, each of the legs having a first end rotatably coupled to one of the band ends and a second end for receiving a hearing protector, wherein the band and pair of legs includes a phosphorescent material, the phosphorescent material being activated by radiant energy to glow-in-the-dark.

11. The phosphorescent hearing protective device of claim 10, wherein the band and pair of legs are formed of a material selected from the group consisting of ABS, polyvinyl chloride, polypropylene, and polyethylene.

12. The phosphorescent hearing protective device of claim 10, wherein the phosphorescent material is disposed on a surface of the band and pair of legs.

13. The phosphorescent hearing protective device of claim 10, wherein the phosphorescent material is dispersed throughout the band and pair of legs.

14. The phosphorescent hearing protective device of claim 10, wherein the phosphorescent material is a zinc sulfide material.

15. The phosphorescent hearing protective device of claim 10, wherein the phosphorescent material is present in an amount from about 3% to about 25% by weight of the total composition.

16. A phosphorescent hearing protective device comprising:
    a foam body; and
    a phosphorescent material integrated into the foam body, wherein the phosphorescent material can be activated by radiant energy to glow-in-the-dark.

17. The phosphorescent hearing protective device of claim 16, wherein the foam is selected from the group consisting of polyurethane, acrylic, acrylic blends, polyvinyl chloride or mixtures thereof.

18. The phosphorescent hearing protective device of claim 16, wherein the phosphorescent material is dispersed throughout the foam body or disposed on an outer surface of the foam body.

19. The phosphorescent hearing protective device of claim 16, wherein the phosphorescent material is present in an amount from about 3% to about 25% by weight of the total composition.

20. A phosphorescent hearing protective device comprising:
    a flexible connecting band having opposing first and second ends; and
    a pair of earmuffs connected to the opposing first and second ends of the connecting band and encompassing an ear of a wearer to attenuate noise, wherein each earmuff has a rigid cup including a phosphorescent material, wherein the phosphorescent material can be activated by radiant energy to glow-in-the-dark.

21. The phosphorescent hearing protective device of claim 20, wherein the phosphorescent material is disposed on a surface of the earmuff cup.

22. The phosphorescent hearing protective device of claim 20, wherein the phosphorescent material is dispersed throughout the earmuff cup.

23. The phosphorescent hearing protective device of claim 20, wherein the phosphorescent material is a zinc sulfide material.

24. The phosphorescent hearing protective device of claim 20, wherein the phosphorescent material is present in an amount from about 3% to about 25% by weight of the total composition.

25. A phosphorescent hearing protective device comprising:
    a flexible connecting band having opposing first and second ends; and
    a pair of earmuffs connected to the opposing first and second ends of the connecting band and encompassing an ear of a wearer to attenuate noise, wherein each earmuff includes a rigid cup and an earmuff cushion secured to the earmuff cup, the earmuff cushion being for contact with an ear of a wearer, the earmuff cushion including a phosphorescent material, wherein the phosphorescent material can be activated by radiant energy to glow-in-the-dark.

* * * * *

UNITED STATES PATENT AND TRADEMARK OFFICE
CERTIFICATE OF CORRECTION

PATENT NO. : 6,095,146
DATED : August 1, 2000
INVENTOR(S) : Richard Knauer et al.

It is certified that error appears in the above-identified patent and that said Letters Patent is hereby corrected as shown below:

<u>Column 8,</u>
Add the following Claims:

-- 26. The phosphorescent hearing protective device of claim 25, wherein the phosphorescent material is disposed on a surface of the earmuff cushion.
27. The phosphorescent hearing protective device of claim 25, wherein the phosphorescent material is dispersed throughout the earmuff cushion.
28. The phosphorescent hearing protective device of claim 25, wherein the phosphorescent material is a zinc sulfide material.
29. The phosphorescent hearing protective device of claim 25, wherein the phosphorescent material is present in an amount from about 3% to about 25% by weight of the total composition. --.

Signed and Sealed this

Nineteenth Day of October, 2004

JON W. DUDAS
*Director of the United States Patent and Trademark Office*